(12) United States Patent
Wu (10) Patent No.: US 8,679,056 B1
(45) Date of Patent: Mar. 25, 2014

(54) SYRINGE

(76) Inventor: Kuo Cheng Wu, Kaohsiung (TW)

(*) Notice: Subject to any disclaimer, the term of this patent is extended or adjusted under 35 U.S.C. 154(b) by 0 days.

(21) Appl. No.: 13/110,036

(22) Filed: May 18, 2011

(51) Int. Cl.
*A61M 37/00* (2006.01)

(52) U.S. Cl.
USPC ............................................. 604/89

(58) Field of Classification Search
USPC ........................................ 604/82, 89
See application file for complete search history.

(56) References Cited

U.S. PATENT DOCUMENTS

| | | | | |
|---|---|---|---|---|
| 5,286,257 | A * | 2/1994 | Fischer ........................... | 604/82 |
| 7,951,108 | B2 * | 5/2011 | Harper et al. .................... | 604/82 |
| 2011/0092902 | A1 | 4/2011 | Kiehne | |
| 2011/0092914 | A1 | 4/2011 | Clayson | |

* cited by examiner

*Primary Examiner* — Matthew F DeSanto
*Assistant Examiner* — Aarti B Berdichevsky
(74) *Attorney, Agent, or Firm* — Alan Kamrath; Kamrath IP Lawfirm, P.A.

(57) ABSTRACT

A syringe including a tube, a first plunger, a second plunger and a plunger rod assembly is disclosed. The tube has one end serving as an injection end and the other end coupled with a cap. The first plunger is disposed in the tube. A filled portion extends through the first plunger. A first chamber is formed between the first plunger and the injection end. The second plunger is disposed in the tube and has a fixing hole. A second chamber is formed between the first and second plungers. The plunger rod assembly comprises a rod and a blocker. The rod has a neck portion and at least one engaging portion. The blocker is arranged on one side of the neck portion and is capable of being inserted into the filled portion. The blocker is capable of being removed from the first plunger and being received in the fixing hole.

11 Claims, 10 Drawing Sheets

FIG. 10 ical to manufacture a disposable syringe 9 that is used
SYRINGE

BACKGROUND OF THE INVENTION

1. Field of the Invention

The present invention generally relates to a syringe and, more particularly, to a syringe that can contain and separate two substances and can mix the two substances before injection.

2. Description of the Related Art

Figure 1:
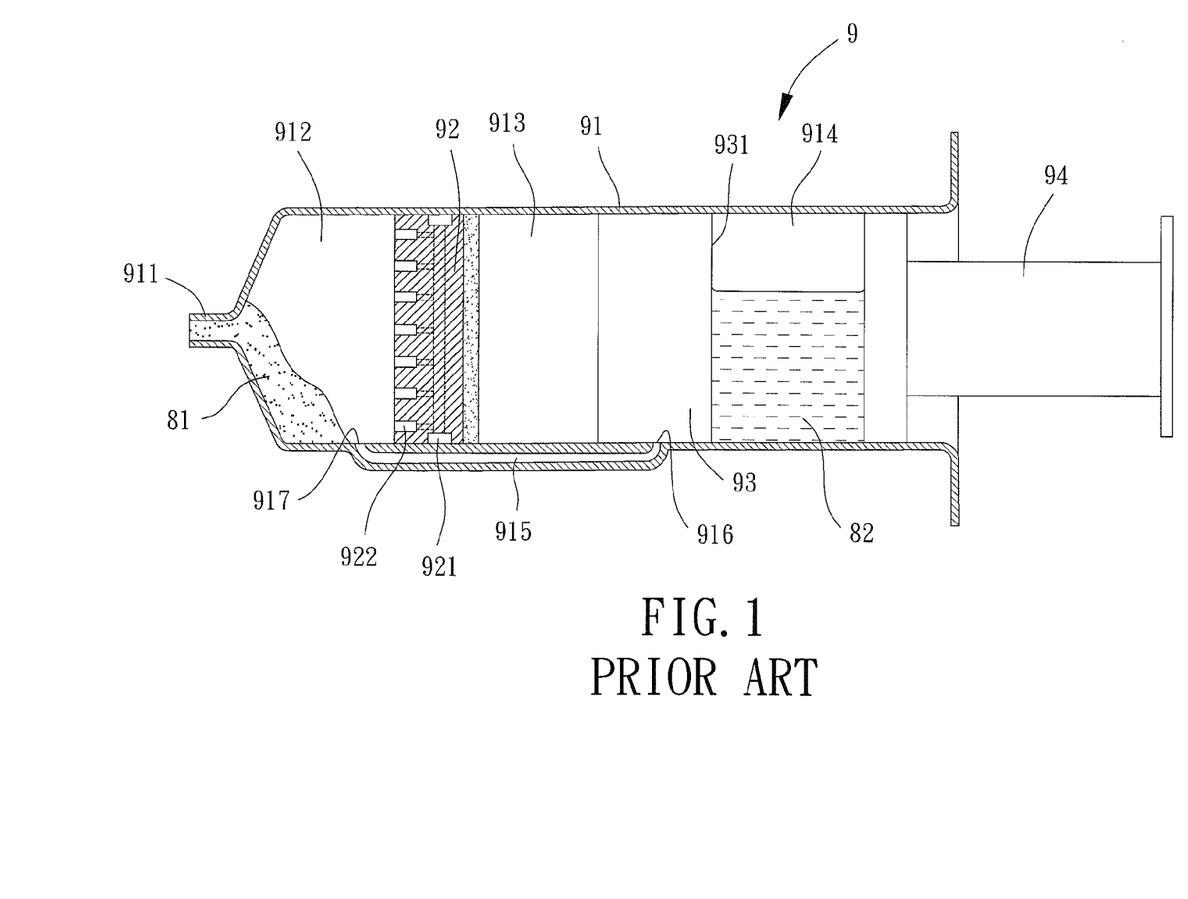
FIG. 1 shows a cross-sectional diagram of a conventional syringe.

Referring to FIG. 1, Taiwanese Patent No. 146251 discloses a syringe 9 including a tube 91, a first partitioning member 92, a second partitioning member 93 and a plunger rod 94. The tube 91 has a nozzle 911 on one end thereof. The first partitioning member 92 and the second partitioning member 93 are received in the tube 91 but spaced from each other. The plunger rod 94 is arranged on the other end of the tube 91. In such an arrangement, the tube 91 will form a first chamber 912 between the nozzle 911 and the first partitioning member 92, a second chamber 913 between the first partitioning member 92 and the second partitioning member 93, and a third chamber 914 between the second partitioning member 93 and the plunger rod 94. The first chamber 912 contains a first drug 81 and the third chamber 914 contains a second drug 82. The tube 91 further includes a by-pass passage 915 having an entrance 916 and an exit 917. The first partitioning member 92 further includes an annular groove 921 and a plurality of axial grooves 922, each having one end communicating with the annular groove 921 and the other end communicating with the first chamber 912.

When the syringe 9 is in use, a user can push the second drug 82, second partitioning member 93 and first partitioning member 92 towards the nozzle 911 by pushing the plunger rod 94. Meanwhile, when a face 931 of the second partitioning member 93 reaches the entrance 916 of the by-pass passage 915, the annular groove 921 will communicate with the exit 917 of the by-pass passage 915. Thus, the second drug 82 in the third chamber 914 will flow into the annular groove 921 of the first partitioning member 92 via the by-pass passage 915. The second drug 82 then enters the first chamber 912 via the axial grooves 922 to mix with the first drug 81.

However, it is difficult to manufacture the syringe 9 as the syringe 9 requires forming the by-pass passage 915, annular groove 921 and axial grooves 922. This significantly increases the manufacturing costs thereof. Especially, it is not economic to manufacture a disposable syringe 9 that is used only once.

SUMMARY OF THE INVENTION

It is therefore the primary objective of this invention to provide a syringe with simple structure and low manufacturing costs.

The invention discloses a syringe including a tube, a first plunger, a second plunger and a plunger rod assembly. The tube has one end serving as an injection end and the other end coupled with a cap. The first plunger is disposed in the tube. A filled portion extends through the first plunger axially, and a first chamber is formed between the first plunger and the injection end. The second plunger is disposed in the tube and has a fixing hole, wherein a second chamber is formed between the first and second plungers. The plunger rod assembly comprises a rod and a blocker. The rod has a neck portion and at least one engaging portion on one end thereof. The blocker is arranged on one side of the neck portion and is capable of being inserted into the filled portion of the first plunger. The blocker is capable of being removed from the first plunger and being received in the fixing hole of the second plunger as the rod moves.

Furthermore, the invention discloses a syringe including a tube, a first plunger, a second plunger and a plunger rod assembly. The tube has one end serving as an injection end and the other end coupled with a cap. The first plunger is disposed in the tube. A filled portion extends through the first plunger axially, and a first chamber is formed between the first plunger and the injection end. The second plunger is disposed in the tube and has a fixing hole, wherein a second chamber is formed between the first and second plungers. The plunger rod assembly comprises a rod and a blocker arranged on one end of the rod. The blocker has at least one engaging portion and is capable of being inserted into the filled portion of the first plunger. The blocker is capable of being removed from the first plunger as the rod moves. The at least one engaging portion of the blocker is capable of being received in the fixing hole of the second plunger.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

In the various figures of the drawings, the same numerals designate the same or similar parts. Furthermore, when the term "first", "second", "third", "fourth", "inner", "outer" "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

Figure 2:
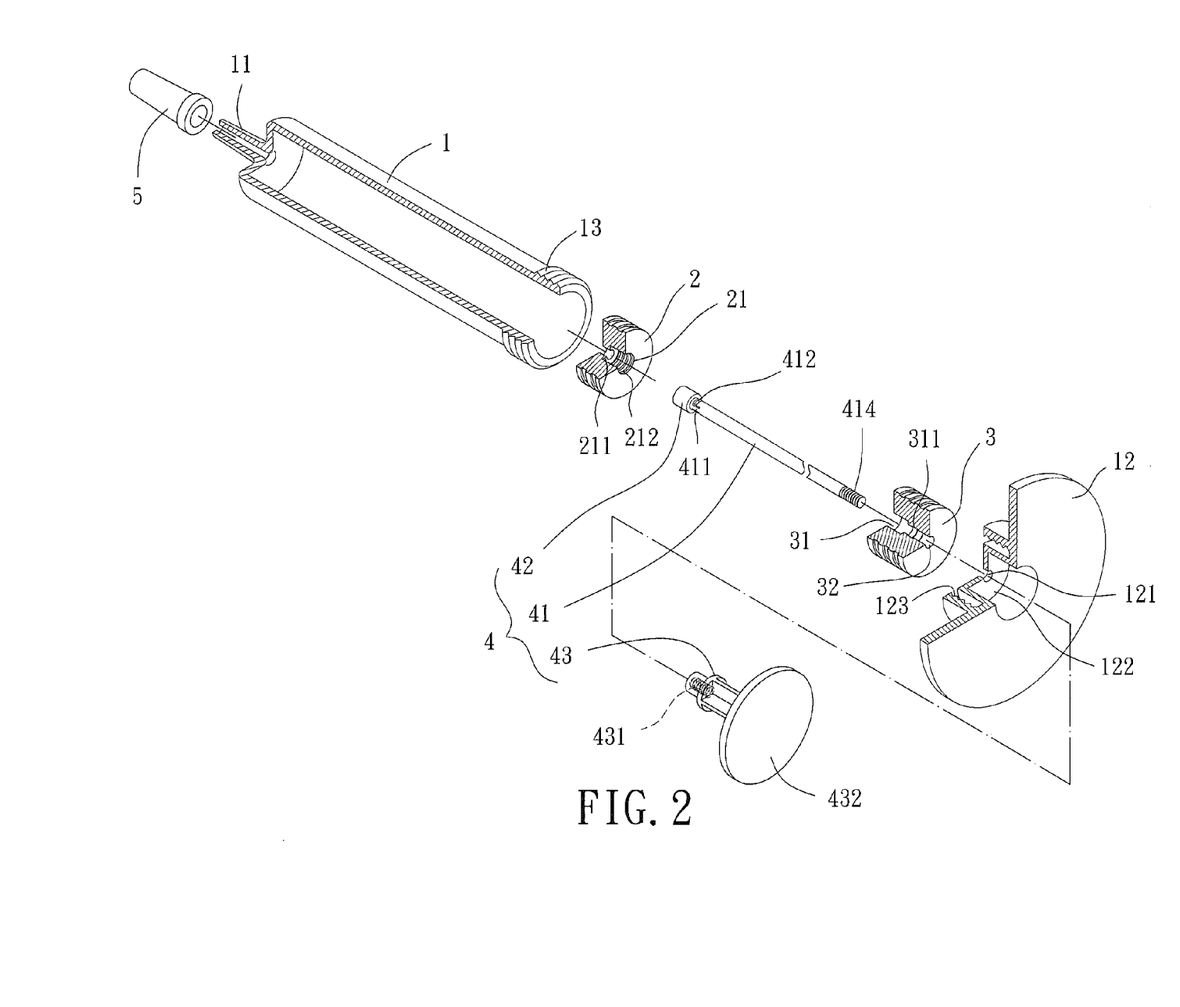
FIG. 2 shows an exploded diagram of a syringe according to a first embodiment of the invention.

FIG. 2 shows an exploded diagram of a syringe according to a first embodiment of the invention. The syringe includes a tube 1, a first plunger 2, a second plunger 3 and a plunger rod assembly 4. The first plunger 2 and second plunger 3 are received in the tube 1 and spaced from each other to define two chambers for accommodation of two substances. The plunger rod assembly 4 controls the communication between the two chambers and drives the second plunger 3 and first plunger 2 to move.

The tube 1 has one end serving as an injection end 11 with increasingly-reduced diameter, as well as the other end coupled with a cap 12 having a through-hole 121. In this embodiment, the cap 12 can have a concave portion 122 and a coupling portion 123 to attain solid coupling between the cap 12 and the tube 1 for better sealing effect of the tube 1.

The concave portion 122 can be stuffed into the tube 1 at one end of the tube 1 and tightly abuts against an inner circumferential wall of the tube 1. The coupling portion 123 may be in the form of inner threads surrounding but spaced from the concave portion 122. The tube 1 may further include a coupling portion 13 at the end where the cap 12 is coupled, wherein the coupling portion 13 may be in the form of outer threads formed on an outer circumferential wall of the tube 1 for threadedly engaging with the inner threads of the coupling portion 123.

Figure 3:
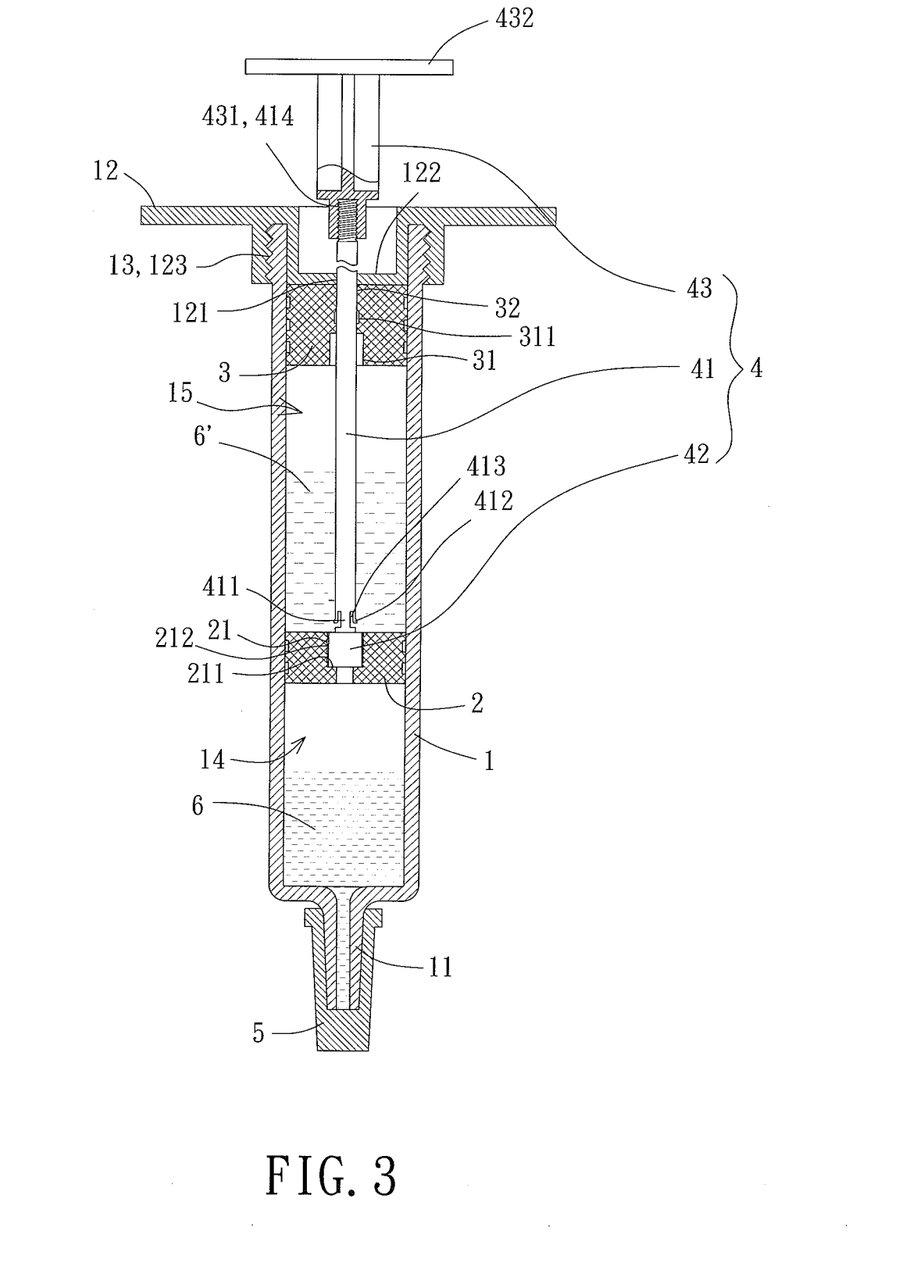
FIG. 3 shows a cross-sectional diagram of the syringe of the first embodiment of the invention.

The first plunger 2 is disposed in the tube 1 so that a first chamber 14 is formed between the first plunger 2 and the injection end 11, as shown in FIG. 3. The first plunger 2 includes a filled portion 21 extending therethrough axially. In the embodiment, the filled portion 21 may be two coaxial holes with different diameter, with a stop face 211 formed between the two holes. The hole with smaller diameter communicates with the first chamber 14. The hole with larger diameter can further include at least one inner protruding ring 212 on an inner circumferential wall thereof.

The second plunger 3 is preferably located in a position close to the cap 12 in the tube 1, so that a second chamber 15 is formed between the second plunger 3 and the first plunger 2, as shown in FIG. 3. The second plunger 3 has a fixing hole 31 communicating with the second chamber 15 and a through-hole 32 communicating with the fixing hole 31, with the fixing hole 31 and the through-hole 32 extending through the second plunger 3 axially. In the embodiment, the second plunger 3 includes a hooking portion 311 annularly arranged in the fixing hole 31.

The plunger rod assembly 4 includes a rod 41 and a blocker 42. The blocker 42 can be coupled with one end of the rod 41 or integrally formed on the rod 41. The other end of the rod 41 extends through the through-hole 32 of the second plunger 3 and the through-hole 121 of the cap 12, and protrudes from the cap 12 of the syringe. Thus, the user can pull the rod 41 to cause movement of the blocker 42 in the second chamber 15. In the embodiment, the blocker 42 is integrally formed on the rod 41, and the end of the rod 41 on which the blocker 42 is formed can form a neck portion 411 and at least one engaging portion 412. The neck portion 411 has a smaller diameter than the rod 41, and the at least one engaging portion 412 can be spaced from each other around the neck portion 411. An annular groove 413 is formed between the neck portion 411 and the at least one engaging portion 412 (as shown in FIG. 3), providing a room for the at least one engaging portion 412 to be bent inwards.

The blocker 42 is designed in a shape fitted to the hole of the filled portion 21 that has a larger diameter. In this embodiment, the blocker 42 may be in a cylindrical form to be stuffed into the filled portion 21. The stop face 211 can prevent the blocker 42 from over-pushing the first plunger 2, avoiding the potential deformation of the first plunger 2 that deteriorates the sealing effect between the first chamber 14 and the second chamber 15.

The plunger rod assembly 4 can further include an auxiliary plunger rod 43 having a connecting portion 431 and a holding portion 432. The end of the rod 41 that protrudes from the cap 12 can form a connecting portion 414 that can be coupled with the connecting portion 431 of the auxiliary plunger rod 43 by ways of screwing or fastening, but is not limited thereto. One skilled in this art may readily appreciate that the connecting portion 414 of the rod 41 may have outer threads and the connecting portion 431 of the auxiliary plunger rod 43 may have corresponding inner threads for mutual screwing when the auxiliary plunger rod 43 is coupled with the rod 41 by way of screwing. The holding portion 432 has a larger cross-sectional area than the rod 41 so that it will be more convenient for the user to hold the holding portion 432 when pushing or pulling the rod 41. Moreover, the auxiliary plunger rod 43 is preferably a cruciform plunger rod with enhanced structural strength, preventing the undesired buckling of the auxiliary plunger rod 43 when the user holds the holding portion 43 for pushing the rod 41 forwards.

FIG. 3 shows an assembly procedure of the syringe of the first embodiment. First, the injection end 11 of the tube 1 is sealed by a sealing member 5. Then, the injection end 11 is faced down and a certain amount of a first pharmaceutical composition 6 is poured into the tube 1. Next, the first plunger 2 is disposed on a predetermined location in the tube 1 to form the first chamber 14. Following, the blocker 42 of the plunger rod assembly 4 is stuffed into the filled portion 21 of the first plunger 2 wherein the coupling between the blocker 42 and the first plunger 2 is secured by the at least one inner protruding ring 212 of the filled portion 21. In this way, the first chamber 14 is fully sealed and the first pharmaceutical composition 6 is well kept in the first chamber 14 without any leakage.

Next, a certain amount of a second pharmaceutical composition 6' is poured into the tube 1, and the second plunger 3 is extended through by the rod 41 and pushed downwards along the rod 41 until it reaches a predetermined location in the tube 1. Thus, the second chamber 15 is formed between the first plunger 2 and the second plunger 3. When the second plunger 3 is disposed in the tube 1, the rod 41 is tightly coupled with a circumferential wall of the through-hole 32 of the second plunger 3. Thus, the second chamber 15 is fully sealed up and the second pharmaceutical composition 6' is well kept in the second chamber 15 without any leakage. It is worth mentioning that one or both of the first pharmaceutical composition 6 and the second pharmaceutical composition 6' are in a liquid form. The neck portion 411 of the rod 41 and the at least one engaging portion 412 can be located in the second chamber 15 when the blocker 42 remains in the filled portion 21 of the first plunger 2.

The through-hole 121 of the cap 12 is then extended through by the rod 41, and the cap 12 is coupled with the coupling portion 13 of the tube 1 via the coupling portion 123 thereof. Thus, the concave portion 122 of the cap 12 can be tightly stuffed into the tube 1 at one end of the tube 1. Next, the auxiliary plunger rod 43 is connected to one end of the rod 41 that protrudes from the tube 1, thereby completing the assembly of the syringe.

Figure 4:
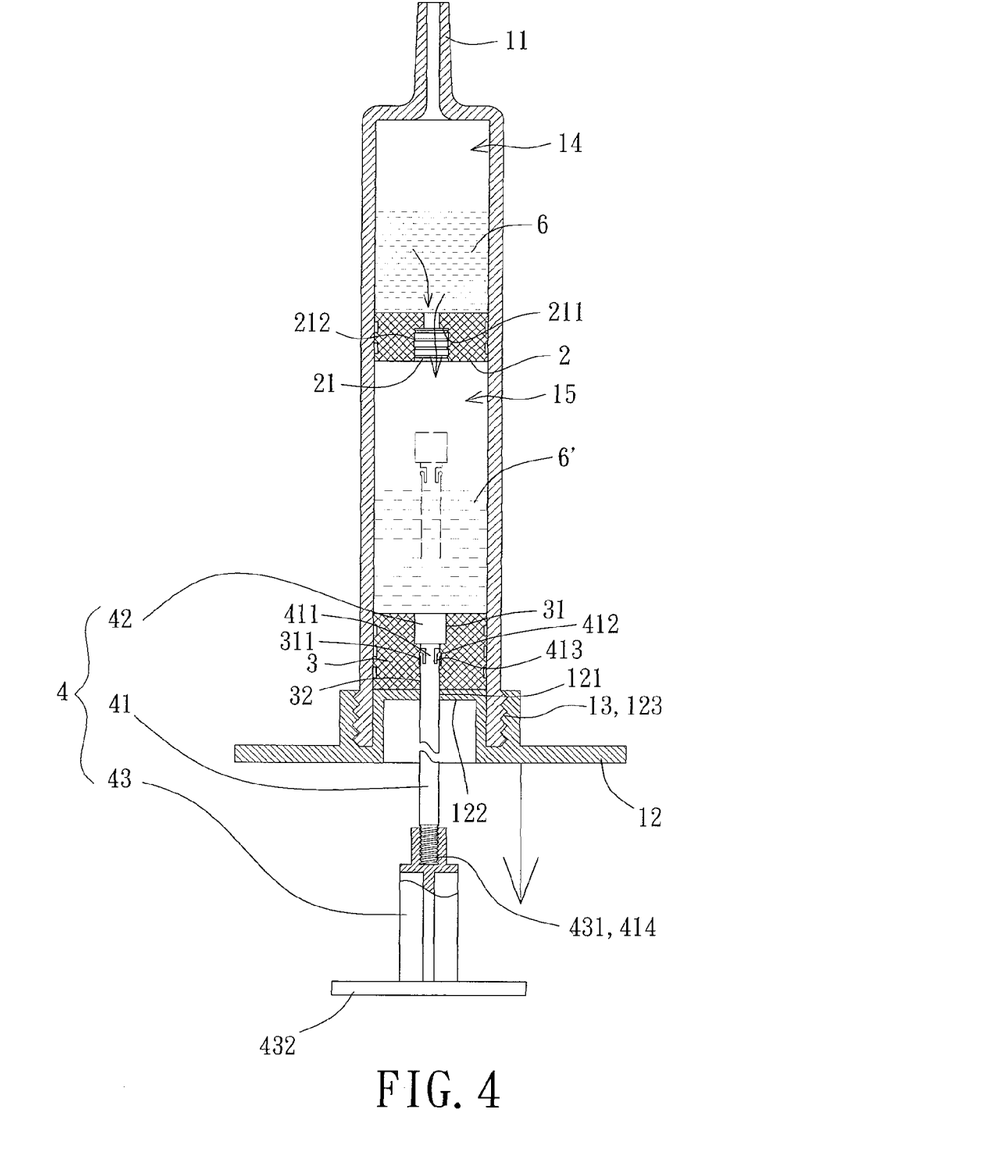
FIG. 4 shows a first operation diagram of the syringe of the first embodiment of the invention.

Referring to FIG. 4, the sealing member 5 shown in FIG. 3 can be removed from the injection end 11 to enable communication between the first chamber 14 and the outside area. Then, the injection end 11 of the tube 1 is faced up, and the blocker 42 of the plunger rod assembly 4 is pulled away from the first plunger 2 to enable communication between the first chamber 14 and the second chamber 15. Therefore, the first pharmaceutical composition 6 in the first chamber 14 can enter the second chamber 15 via the first plunger 2 to mix with the second pharmaceutical composition 6'. When the at least one engaging portion 412 of the rod 41 enters the fixing hole 31 of the second plunger 3, the at least one engaging portion 412 will be squeezed by a circumferential wall of the fixing hole 31 and therefore be bent inwards towards the annular groove 413. When the least one engaging portion 412 enters and sticks in the hooking portion 311 of the second plunger 3, the at least one engaging portion 412 will bounce back to where it was and the blocker 42 can remain in the fixing hole 31 of the second plunger 3. At this time, the at least one engaging portion 412 of the rod 41 can abut against the hooking portion 311 of the second plunger 3, avoiding the blocker 42 from escaping from the second plunger 3.

Figure 5:
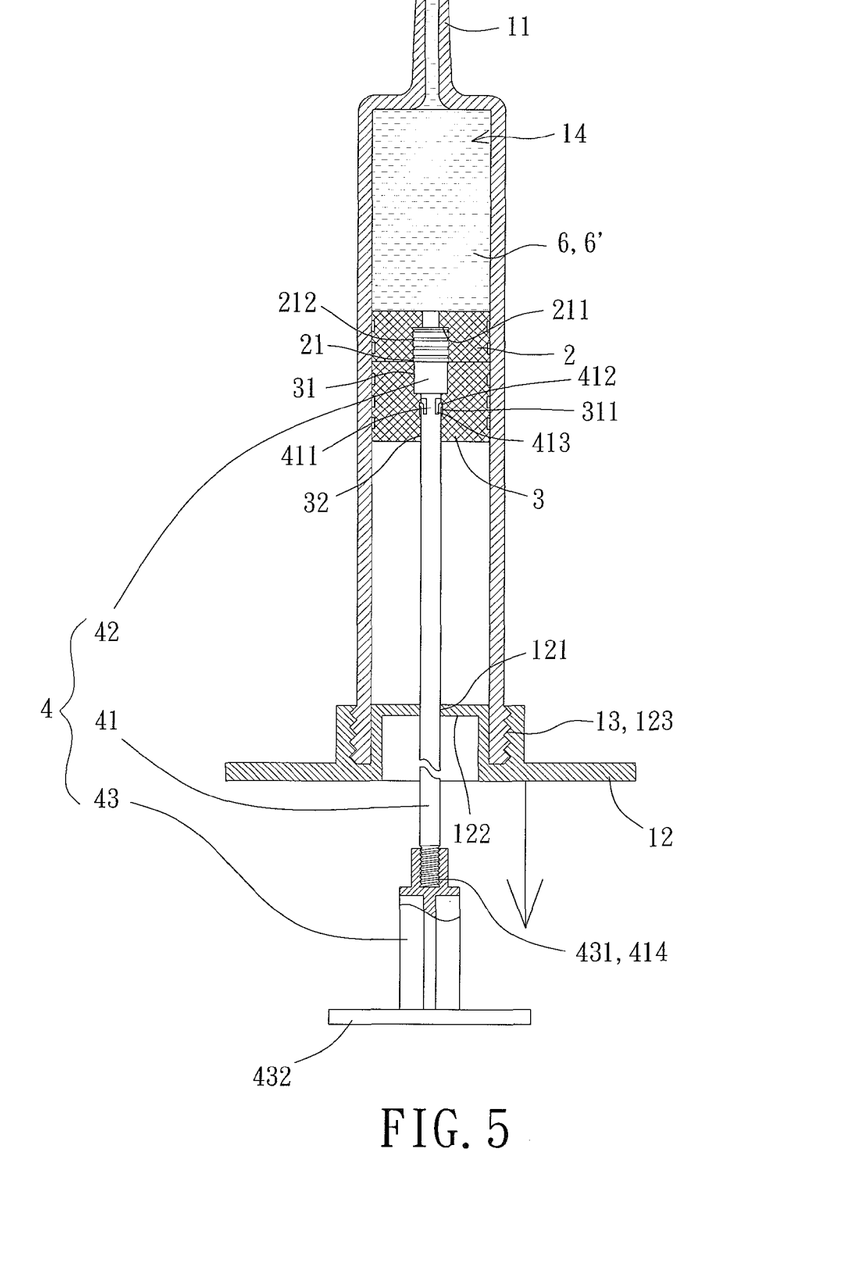
FIG. 5 shows a second operation diagram of the syringe of the first embodiment of the invention.

Referring to FIG. 5, after the blocker 42 is fixed in the second plunger 3, the plunger rod assembly 4 can push the second plunger 3 towards the injection end 11 when the user applies force to the auxiliary plunger rod 43. As a result, the plunger rod assembly 4 will squeeze the second chamber 15, forcing a mixture of the first pharmaceutical composition 6 and the second pharmaceutical composition 6' to flow from the second chamber 15 into the first chamber 14 via the filled portion 21 of the first plunger 2.

Figure 6:
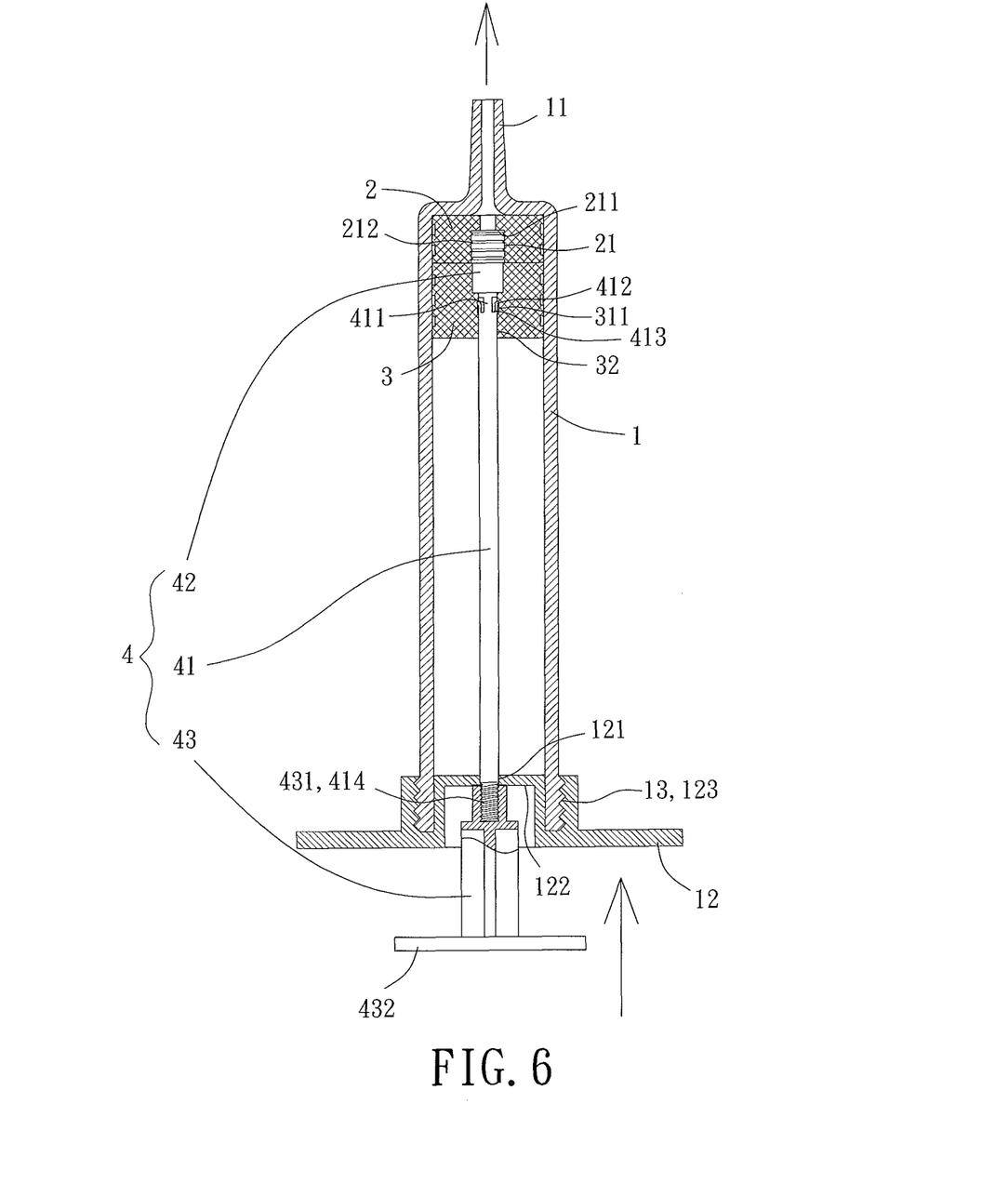
FIG. 6 shows a third operation diagram of the syringe of the first embodiment of the invention.

Referring to FIG. 6, when the second plunger 3 touches the first plunger 2, the user can keep pushing the auxiliary plunger rod 43 so that the second plunger 3 can drive the first plunger 2 to move towards the injection end 11. Thus, the mixture of the first pharmaceutical composition 6 and the second pharmaceutical composition 6' in the first chamber 14 can be forced out of the injection end 11 until the first plunger 2 reaches the end of the tube 1.

Figure 7:
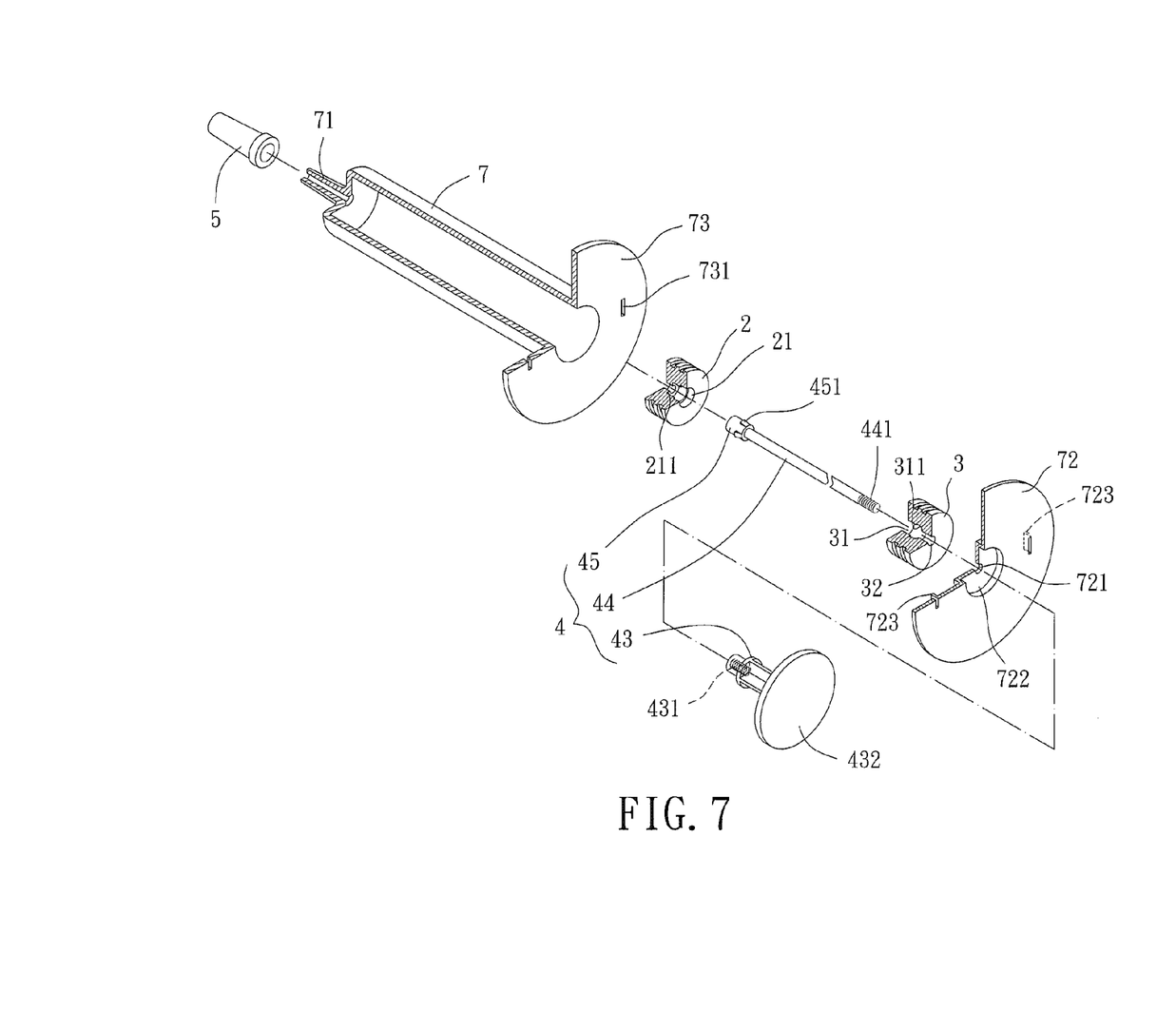
FIG. 7 shows an exploded diagram of a syringe according to a second embodiment of the invention.
Figure 8:
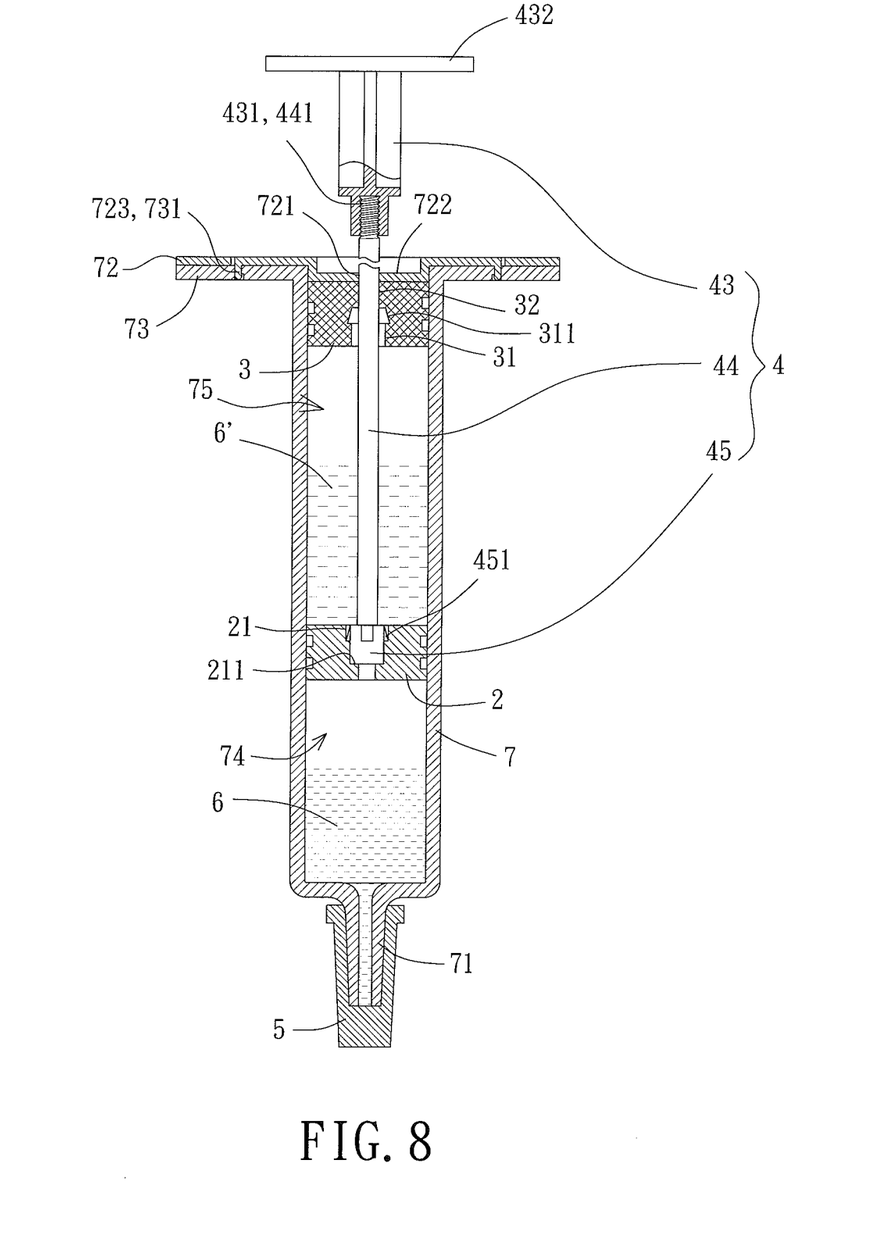
FIG. 8 shows a cross-sectional diagram of the syringe of the second embodiment of the invention.

FIGS. 7 and 8 show an exploded diagram and a cross-sectional diagram of a syringe according to a second embodiment of the invention. The syringe of the second embodiment includes a tube 7 that is different from the tube 1 in the first embodiment. The tube 7 has one end formed as an injection end 71 with increasingly-reduced diameter, as well as the other end coupled with a cap 72 having a through-hole 721. In this embodiment, the cap 72 can have a concave portion 722 and at least one coupling portion 723 to attain solid coupling between the cap 72 and the tube 7 for better sealing effect of the tube 7. The concave portion 722 can be stuffed into the tube 7 at one end of the tube 7 and tightly abuts against an inner circumferential wall of the tube 7. The at least one coupling portion 723 may be a single protrusion or a plurality of protrusions spaced from each other around the concave portion 722. Moreover, the tube 7 can form a protruding ring 73 at the end thereof where the cap 72 is coupled, with the protruding ring 73 having at least one coupling portion 731 in the form of, for example, a groove. The at least one coupling portion 731 corresponds to the at least one coupling portion 723 of the cap 72 in terms of quantity and location, such that the at least one coupling portion 731 can couple with the at least one coupling portion 723. Also, the protruding ring 73 may be held by the user for convenient operation of the syringe.

The components of the syringe in the second embodiment that have the same structures as those in the first embodiment will not be described herein again for brevity. However, the plunger rod assembly 4 in the second embodiment includes a rod 44 and a blocker 45 coupled with one end of the rod 44. The other end of the rod 44 extends through the through-hole 32 of the second plunger 3 and the through-hole 121 of the cap 12, and protrudes from the cap 12 of the syringe. The end of the rod 44 that protrudes from the cap 12 can form a connecting portion 441 that can be coupled with the connecting portion 431 of the auxiliary plunger rod 43. The blocker 45 includes at least one engaging portion 451 that can be annularly arranged on an outer circumferential face thereof. The at least one engaging portion 451 has a shape corresponding to the shape of the hooking portion 311 of the second plunger 3. The shape of the filled portion 21 of the first plunger 2 also corresponds to that of the at least one engaging portion 451.

Therefore, the user can pull the blocker 45 of the plunger rod assembly 4 away from the filled portion 21 of the first plunger 2 by pulling the auxiliary plunger rod 43. Then, the blocker 45 of the plunger rod assembly 4 is inserted into the fixing hole 31 of the second plunger 3, allowing the at least one engaging portion 451 of the blocker 45 to abut against the hooking portion 311 of the second plunger 3. Thus, the blocker 45 cannot escape from the second plunger 3, thereby providing desired coupling effect between the blocker 45 and the second plunger 3.

Figure 9:
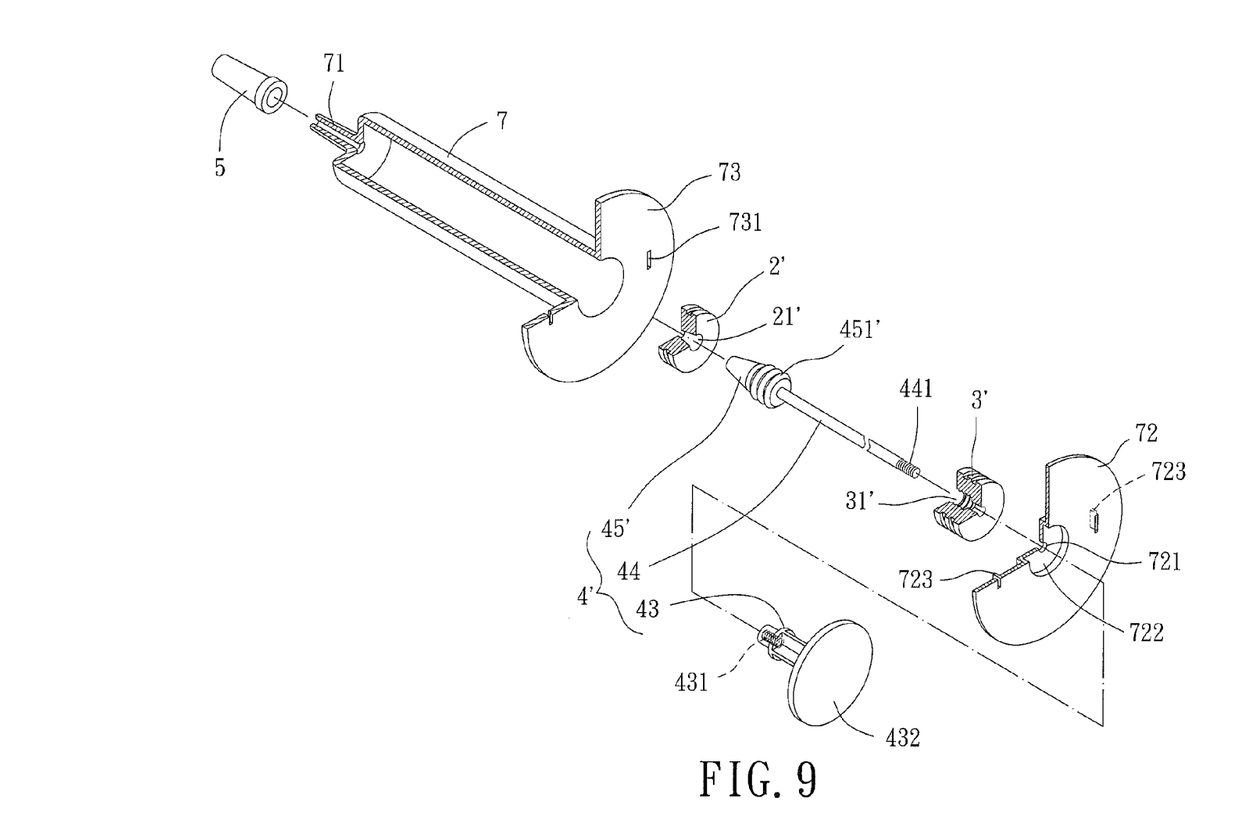
FIG. 9 shows an exploded diagram of a syringe according to a third embodiment of the invention.
Figure 10:
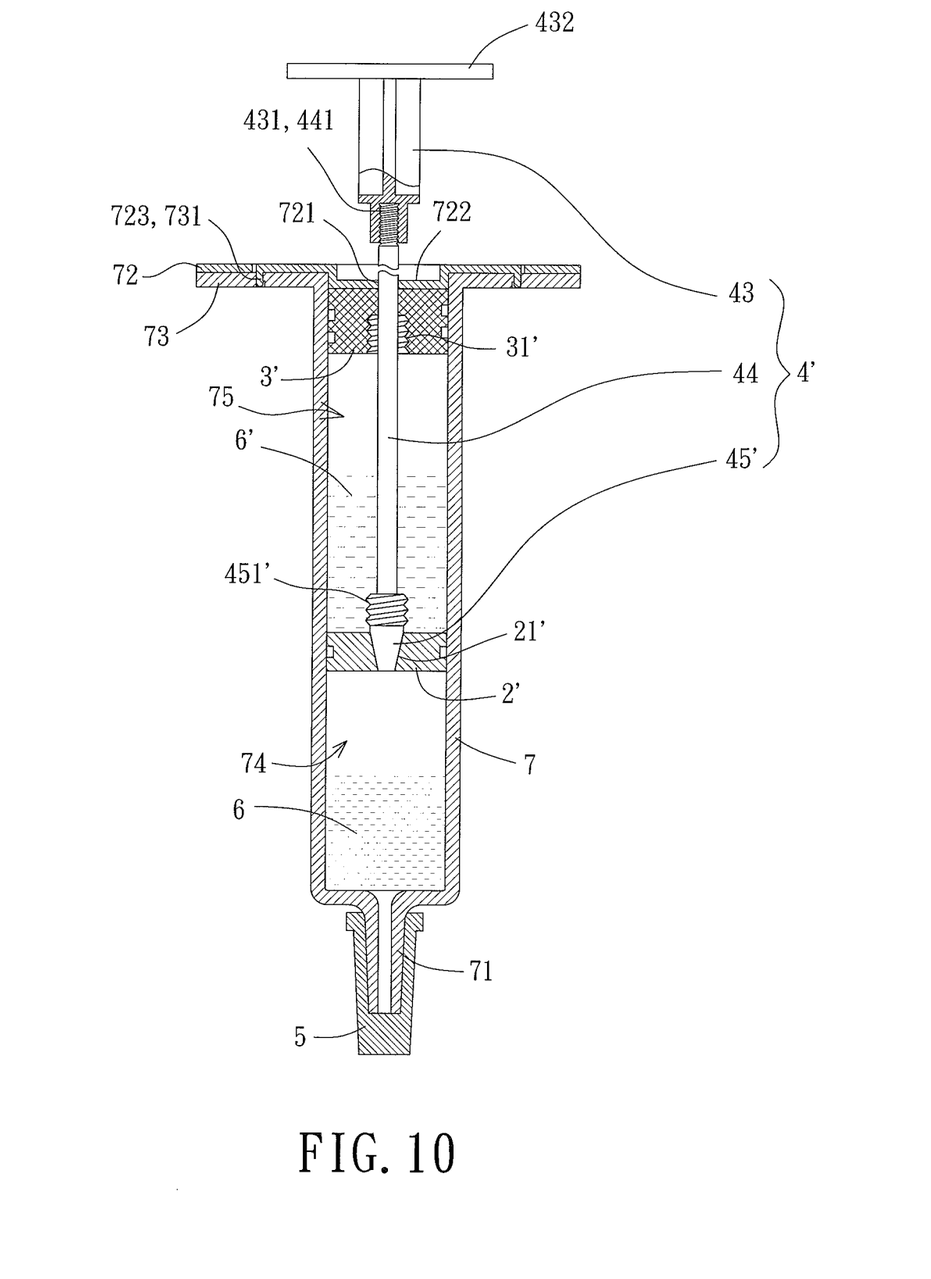
FIG. 10 shows a cross-sectional diagram of the syringe of the third embodiment of the invention.

FIGS. 9 and 10 show an exploded diagram and a cross-sectional diagram of a syringe according to a third embodiment of the invention. The syringe of the third embodiment differs from those of the previous embodiments in that the syringe includes a first plunger 2' having a filled portion 21' in the form of a tapered hole with increasingly-reduced diameter towards the injection end 71 of the tube 7. Besides, the syringe also includes a second plunger 3' having a fixing hole 31' with inner threads. The syringe also includes a plunger rod assembly 4' having a blocker 45', wherein the blocker 45' has one end with tapered form corresponding to the tapered filled portion 21' of the first plunger 2', as well as the other end with outer threads (which is defined as an engaging portion 451'). The blocker 45' of the plunger rod assembly 4' can be stuffed into the filled portion 21' of the first plunger 2'. Thus, the further the blocker 45' is inserted into the filled portion 21', the tighter the first plunger 2' couples with both the blocker 45' and the inner circumferential wall of the tube 7. In this way, the first chamber 14 can be well sealed.

Besides, the user can pull the blocker 45' away from the filled portion 21' when it is desired. Therefore, the blocker 45' will finally touch the second plunger 3'. At this point, the user can screw the engaging portion 451' (that has outer threads) to the fixing hole 31' of the second plunger 3' (that has inner threads) by twisting the auxiliary plunger rod 43. This prevents the blocker 45' from escaping from the second plunger 3'. By screwing the blocker 45' and the second plunger 3' together, the coupling between the blocker 45' and the second plunger 3' can be strengthened. Furthermore, when the second plunger 3' approaches the first plunger 2', the tapered end of the blocker 45' can be re-inserted into the filled portion 21' of the first plunger 2', avoiding the mixture from remaining between the second plunger 3' and the first plunger 2'.

In conclusion, each component of the syringe of the invention has a simpler structure than the conventional one, thus significantly reducing the costs of the syringe. Thus, it will be cost-effective to manufacture a disposable one.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A syringe, comprising:
 a tube having one end serving as an injection end and the other end coupled with a cap;
 a first plunger disposed in the tube, wherein a filled portion axially extends through the first plunger, and a first chamber is formed between the first plunger and the injection end;
 a second plunger disposed in the tube and having a fixing hole, wherein a second chamber is formed between the first and second plungers; and
 a plunger rod assembly comprising a rod and a blocker, wherein the rod has a neck portion and at least one engaging portion on one end of the rod, the blocker is arranged on one side of the neck portion and is capable of being inserted into the filled portion of the first plunger, and the blocker is capable of being removed from the first plunger and being received in the fixing hole of the second plunger as the rod moves.

2. The syringe as claimed in claim 1, wherein the at least one engaging portion is comprised of multiple engaging portions that are spaced from each other around the neck portion while an annular groove is formed between the neck portion and the at least one engaging portion.

3. A syringe, comprising:
a tube having one end serving as an injection end and the other end coupled with a cap;
a first plunger disposed in the tube, wherein a filled portion axially extends through the first plunger, and a first chamber is formed between the first plunger and the injection end;
a second plunger disposed in the tube and having a fixing hole, wherein a second chamber is formed between the first and second plungers; and
a plunger rod assembly comprising a rod and a blocker arranged on one end of the rod, wherein the blocker has at least one engaging portion and is capable of being inserted into the filled portion of the first plunger, the blocker is capable of being removed from the first plunger as the rod moves, and the at least one engaging portion of the blocker is capable of being received in the fixing hole of the second plunger.

4. The syringe as claimed in claim 3, wherein the filled portion of the first plunger is a tapered hole with an increasingly-reduced diameter towards the injection end of the tube, and a front part of the blocker has a tapered form corresponding to the tapered hole of the first plunger.

5. The syringe as claimed in claim 3, wherein the filled portion of the first plunger comprises two coaxial holes, where a first coaxial hole has a smaller diameter and a second coaxial hole has a larger diameter, while a stop face is formed between the two coaxial holes, the coaxial hole with smaller diameter communicates with the first chamber, and a front part of the blocker has a shape fitted to the coaxial hole with larger diameter.

6. The syringe as claimed in claim 5, wherein the second plunger includes a hooking portion annularly arranged in the fixing hole, and the at least one engaging portion of the blocker is annularly arranged on an outer circumferential face of the blocker, and has a shape corresponding to the shape of the hooking portion of the second plunger.

7. The syringe as claimed in claim 5, wherein the fixing hole of the second plunger has inner threads and the at least one engaging portion of the blocker has outer threads.

8. The syringe as claimed in claim 5, wherein one end of the rod protrudes from the second plunger and the cap to form a connecting portion, the plunger rod assembly further includes an auxiliary plunger rod having a holding portion and a connecting portion coupled with the connecting portion of the rod.

9. The syringe as claimed in claim 5, wherein the tube forms a protruding ring at the end thereof where the cap is coupled, the protruding ring has at least one coupling portion, the cap has a concave portion and at least one coupling portion coupled with the at least one coupling portion of the protruding ring, and the concave portion is stuffed into the tube at one end of the tube and tightly abuts against an inner circumferential wall of the tube.

10. The syringe as claimed in claim 5, wherein the tube further includes a coupling portion at the end where the cap is coupled, the cap has a concave portion and a coupling portion surrounding but spaced from the concave portion, the concave portion is stuffed into the tube at one end of the tube and tightly abuts against an inner circumferential wall of the tube, and the coupling portion of the cap is coupled with the coupling portion of the tube.

11. The syringe as claimed in claim 5, wherein the filled portion further includes at least one inner protruding ring on an inner circumferential wall thereof.

* * * * *